United States Patent
Yamauchi et al.

(10) Patent No.: US 7,041,713 B2
(45) Date of Patent: May 9, 2006

(54) ARTIFICIAL DURA MATER

(75) Inventors: Koji Yamauchi, Ayabe (JP); Tomohiko Asahara, Tokyo (JP)

(73) Assignee: Gunze Limited, Kyoto (JP)

( * ) Notice: Subject to any disclaimer, the term of this patent is extended or adjusted under 35 U.S.C. 154(b) by 32 days.

(21) Appl. No.: 10/019,754

(22) PCT Filed: Apr. 27, 2001

(86) PCT No.: PCT/JP01/03688

§ 371 (c)(1),
(2), (4) Date: Apr. 30, 2002

(87) PCT Pub. No.: WO01/82990

PCT Pub. Date: Nov. 8, 2001

(65) Prior Publication Data

US 2002/0183856 A1    Dec. 5, 2002

(30) Foreign Application Priority Data

Apr. 28, 2000    (JP) .............................. 2000-130676

(51) Int. Cl.
*A61F 2/02*    (2006.01)
*C08K 9/00*    (2006.01)

(52) U.S. Cl. ...................... 523/113; 523/105; 523/206; 623/11.11; 623/23.75; 623/926

(58) Field of Classification Search ................ 523/105, 523/206, 113; 623/11.11, 23.75, 926
See application file for complete search history.

(56) References Cited

U.S. PATENT DOCUMENTS

| | | |
|---|---|---|
| 4,045,418 A | 8/1977 | Sinclair |
| 4,364,126 A * | 12/1982 | Rosen et al. ............... 623/2.38 |
| 4,643,734 A | 2/1987 | Lin |
| 4,968,317 A | 11/1990 | Tormala et al. |
| 5,234,456 A | 8/1993 | Silvestrini |
| 5,634,944 A | 6/1997 | Magram |
| 5,861,034 A | 1/1999 | Taira et al. |
| 6,514,291 B1 * | 2/2003 | Yamauchi et al. ....... 623/23.72 |
| 6,548,569 B1 * | 4/2003 | Williams et al. ........... 523/124 |

FOREIGN PATENT DOCUMENTS

| | | |
|---|---|---|
| EP | 0274898 | 7/1988 |
| EP | 0423155 | 11/1994 |
| EP | 1029553 | 8/2000 |
| GB | 22222954 | 3/1990 |
| JP | 63-103643 | 7/1988 |
| JP | 64-2383 | 1/1989 |
| JP | 2-152461 | 6/1990 |
| JP | 3-505535 | 12/1991 |
| JP | 9-140785 | 6/1997 |
| JP | 8-80344 | 3/1998 |
| JP | 2000-93499 | 4/2000 |
| WO | WO 90/00410 | 1/1990 |
| WO | WO 92/04393 | 3/1992 |
| WO | WO 99/20320 | 4/1999 |

OTHER PUBLICATIONS

Nikaido, et al. (1994) *Fibrin Glue.* Japan Pharmacol. Ther., 22 (2) 329-337.

Miyazaki, et al. (1969) *Fundamental and Clinical Studies on the Absorbable Gelatin Film as Dural Substitute.* Handbook of Clinical Neurology 21: 1089-1098.

Collins, R.L.L., et al. (1991) *Use of collagen film as a dural substitute: Preliminary animal studies.* J. Biomed. Materials Research 25:267-276.

Takayama, et al. (1993) *Creutzfeldt-Jakob Disease transmitted by cadaveric dural graft: A case report.* Noshinkeigaka 21(2) 167-170.

Co-pending Application, U.S. Appl. No. 09/529,758, filed Apr. 6, 2000.

Co-pending Application, U.S. Appl. No. 09/529,073, filed Apr. 19, 2000.

* cited by examiner

*Primary Examiner*—Tae H. Yoon
(74) *Attorney, Agent, or Firm*—Knobbe, Martens, Olson & Bear, LLP

(57) ABSTRACT

The present invention provides an artificial dura mater which comprises an amorphous or low crystallinity polymer as a constituent component and which prevents the cerebrospinal fluid leakage.

14 Claims, No Drawings

ARTIFICIAL DURA MATER

RELATED APPLICATIONS

This is the U.S. National Phase under 35 U.S.C. § 371 of International Application No. PCT/JP01/03688, filed Apr. 27, 2001, which claims priority to Japanese Application No. 2000-130676, filed Apr. 28, 2000.

TECHNICAL FIELD

This invention relates to the field of neurosurgery. In particular, the present invention relates to an artificial dura mater for use in medical implants.

BACKGROUND ART

The dura mater is located between the cranium and the brain and around the spinal cord. It principally protects the brain and spinal cord and prevents cerebrospinal fluid leakage. Defects or contractures of the dura mater need to be compensated for and lyophilized human dura mater has been used for that purpose. However, human dura mater has drawbacks such as low homogeneity and limited supply. Further, possible transmission of Creutzfeldt-Jakob disease through the use of human dura mater was reported (Noshinkeigeka; 21(2), 167–170, 1993) and, eventually, the Japanese Ministry of Health and Welfare banned the use of lyophilized human dura mater on Apr. 7, 1997.

To solve the above problems, an artificial dura mater made of silicone was developed. However, silicone dura mater has fallen into disuse as it was reported that silicone dura mater creates a predisposition to meningorrhagia by remaining permanently in vivo because it is non-biodegradable, chronically stimulating the surrounding tissue and causing hypertrophy of the granulation tissue.

In contrast, artificial dura maters made of biodegradable and bioabsorbable materials such as collagen (Journal of Biomedical Materials Research; Vol. 25 267–276, 1991) and gelatin (No to Shinkei; 21 1089–1098, 1969) were produced, but they are not in practical use because of strength-related problems, i.e., because their suture strength is insufficient to allow them to be sutured integrally with the dura mater.

The applicant provided, in Japanese Unexamined Patent Publication No. 1996-80344, not only an artificial dura mater comprising a sheet made of a biodegradable and bioabsorbable polymer, for example, a copolymer of lactic acid and caprolactone, but also an artificial dura mater further comprising a biodegradable and bioabsorbable polymer made of a material different from that of the sheet as reinforcement between sheets and an integral molding of the sheets and the reinforcement.

The applicant also provided an artificial dura mater which showed improved non-leakage and suture strength, etc. and a production method thereof, as well as an artificial dura mater which allows optical observation of the brain inside.

However, the criteria of flexibility, inhibition of the cerebrospinal fluid leakage, and mechanical strength, etc. required in the artificial dura mater when used medically were not discussed in detail.

An object of the present invention is to additionally propose the constituent components necessary for an artificial dura mater and their properties.

DISCLOSURE OF INVENTION

The present invention provides the items 1 to 19 listed below.

Item 1. An artificial dura mater comprising an amorphous or low crystallinity polymer.

Item 2. The artificial dura mater according to item 1 wherein the polymer has a degree of crystallinity of 20% or lower.

Item 3. An artificial dura mater which is formed as an integral molding of an amorphous or low crystallinity polymer and a structural reinforcement.

Item 4. The artificial dura mater according to item 3 wherein the amorphous or low crystallinity polymer and the structural reinforcement are integrated by bonding, fusion or impregnation.

Item 5. The artificial dura mater according to item 1 wherein the elastic modulus of the amorphous or low crystallinity polymer at 5% extension is 10 MPa or lower.

Item 6. The artificial dura mater according to item 1 wherein the Tg of the amorphous or low crystallinity polymer is 15° C. or lower.

Item 7. The artificial dura mater according to item 1 wherein the tensile elongation at break of the amorphous or low crystallinity polymer is 200% or greater.

Item 8. The artificial dura mater according to item 1 wherein the elastic modulus of the amorphous or low crystallinity polymer at 37° C. is $1 \times 10^8$ Pa or less.

Item 9. The artificial dura mater according to item 1 wherein the ratio of relaxation elastic modulus/elastic modulus is 0.3 or greater.

Item 10. The artificial dura mater according to item 3 wherein the elastic modulus of the structural reinforcement at 5% extension is greater than 10 MPa.

Item 11. The artificial dura mater according to item 3 wherein the Tg of the structural reinforcement is higher than 15° C.

Item 12. The artificial dura mater according to item 3 wherein the tensile elongation at break of the structural reinforcement is less than 200%.

Item 13. The artificial dura mater according to item 3 wherein the weight of the amorphous or low crystallinity polymer is 10 to 98% of the total weight of the integral molding.

Item 14. The artificial dura mater according to item 3 wherein the weight of the structural reinforcement is 2% or more of the total weight of the integral molding.

Item 15. The artificial dura mater according to item 1 wherein the amorphous or low crystallinity polymer is biodegradable.

Item 16. The artificial dura mater according to item 3 wherein the structural reinforcement is biodegradable.

Item 17. The artificial dura mater according to item 3 wherein the amorphous or low crystallinity polymer is biodegradable and the structural reinforcement is non-biodegradable.

Item 18. The artificial dura mater according to item 3 wherein the structural reinforcement is non-biodegradable.

Item 19. The artificial dura mater according to item 3 wherein the amorphous or low crystallinity polymer is non-biodegradable and the structural reinforcement is biodegradable.

The amorphous or low crystallinity polymer of the invention has the flexibility required in an artificial dura mater and prevents cerebrospinal fluid leakage. The degree of crystallinity is preferably 20% or lower. Having a considerably high degree of crystallinity improves its mechanical strength; however, the resultant polymer will be too rigid and liable to damage the brain surface and making a watertight suture with the surrounding tissue will become difficult.

The elastic modulus at 5% extension preferably does not exceed 10 MPa, and more preferably is 8.5 MPa or less. A polymer having an elastic modulus in the above-mentioned range is flexible enough to easily conform to the surrounding tissue. On the other hand, when the elastic modulus is unduly high, the polymer will be so rigid as to risk damaging the brain surface. The relaxation elastic modulus is preferably 30% or more of the elastic modulus (the ratio of relaxation elastic modulus/elastic modulus is 0.3 or greater), and more preferably 50% or more (the ratio of relaxation elastic modulus/elastic modulus is 0.5 or greater). A polymer having a higher relaxation elastic modulus exhibits lower plasticity. Such a polymer undergoes elastic deformation, hence only limited expansion of pinholes is observed after suturing. On the other hand, when the relaxation elastic modulus is low, the polymer significantly deforms when external force is applied, which undesirably allows pinholes to remain after suturing and may lead to cerebrospinal fluid leakage. Even when a material having a low elastic modulus is used, if the relaxation elastic modulus thereof is low, expansion of pinholes and the like occur, therefore satisfactory prevention of cerebrospinal fluid leakage, required in an artificial dura mater, is unobtainable. When the material of the invention, having a low elastic modulus and a high relaxation elastic modulus, is used as a part of an artificial dura mater, a flexible artificial dura mater that satisfactorily prevents cerebrospinal fluid leakage is obtained.

Medical instruments are used under temperatures from 30° C., for the treatment of hypothermia, to 45° C., when treating local pyrexia. Accordingly, the glass transition point thereof is preferably 15° C. or lower, more preferably 0° C. or lower. A polymer becomes rigid below its glass transition point, therefore a polymer requiring enough flexibility to be usable as an implant should have a glass transition point lower than the operating temperature.

The tensile elongation at break is preferably 200% or greater, and more preferably 500% or greater. Dura mater having a low tensile elongation at break will break during implantation since it is subjected to suturing under tension.

The amorphous or low crystallinity polymer of the invention is composed of one or more members selected from sheet, films sponge, cord, nonwoven fabric substance and knitted/woven fabric. Since the polymer must prevent cerebrospinal fluid leakage, it is preferably a film, discontinuous foam sponge or the like.

Even when the aforementioned amorphous or low crystallinity polymer is flexibile and prevents cerebrospinal fluid leakage to the extent required in an artificial dura mater, handling difficulties may arise in some cases where suturing cannot be conducted or the artificial dura mater is incapable of enduring the intracranial pressure. Accordingly, it is desirable that the artificial dura mater be reinforced with a structural reinforcement. The structural reinforcement is composed of one or more members selected from fabric, cord, nonwoven fabric substance, knitted/woven fabric, sheet and film. The structural reinforcement improves the strength of the artificial dura mater; however, when the content of the structural reinforcement in the artificial dura mater is unduly large, although the strength improves, the artificial dura mater becomes too rigid. Therefore, the minimum necessary amount of the structural reinforcement is desirably used. When the amorphous or low crystallinity polymer is integrally molded with the structural reinforcement to form one united body, layers of the amorphous or low crystallinity polymer and the structural reinforcement are united in alternation. It is also possible to integrate them by forming a multilayer structure in such a manner that the structural reinforcement layers are inserted into the layers of amorphous or low crystallinity polymer and these groups of layers are united.

The object of the invention can be achieved by impregnating the structural reinforcement with an amorphous or low crystallinity polymer solution and removing the solvent whereby the amorphous or low crystallinity polymer layer and the structural reinforcement layer are integrated into one unit without forming another layer in between.

The elastic modulus of the structural reinforcement at 5% extension is preferably above 10 MPa, more preferably 50 MPa or higher. When the elastic modulus is low, the integrally molded artificial dura mater has insufficient suture strength and pinholes are liable to expand, which may lead to cerebrospinal fluid leakage. Having a high elastic modulus can prevent the artificial dura mater with integrated structural reinforcement from expanding or deforming too much.

The Tg of the structural reinforcement is preferably above 15° C. when the Tg is below 15° C., the structural reinforcement tends to deform under body temperature. The structural reinforcement of the invention maintains the form of the integrally molded artificial dura mater, therefore deformation of the structural reinforcement itself is undesirable. When the Tg of the structural reinforcement is above 15° C., even if the artificial dura mater is warmed by body temperature during surgery the integrally molded artificial dura mater has a certain stiffness and does not become too flexible, thus trimming and suturing are easily conducted.

The tensile elongation at break of the structural reinforcement is preferably less than 200%. When tensile stress is high, the integrally molded artificial dura mater is liable to deform since it has high tensile elongation, which may cause cerebrospinal fluid leakage through the sutural portions. When the tensile elongation at break of the structural reinforcement is low, the integrally molded artificial dura mater has a high tensile elongation on a microscopic level due to the amorphous or low crystallinity polymer, at the same time, the tensile elongation on a macroscopic level is kept down because of the structural reinforcement. This is desirable Using bioabsorbable amorphous or low crystallinity polymer and a structural reinforcement made of bioabsorbable polymer can provide a bioabsorbable artificial dura mater. When the at least one of the two is made of non-bioabsorbable polymer, only the non-bioabsorbable polymer will remain in vivo. When both are made of non-bioabsorbable polymer, the resultant artificial dura mater will be non-bioabsorbable The weight content of the amorphous or low crystallinity polymer in the integral molding with the structural reinforcement is generally about 10 to 98%, and preferably about 50 to 98%.

The content of the structural reinforcement in the integral molding is generally about 2% by weight or higher, and preferably about 2 to 10% by weight.

In the above structure, examples of biodegradable polymers include aliphatic polyesters (polyglycolic acid, polylactic acid, polycaprolactone, polyvalerolactone and copolymers thereof), polyesterethers (poly-1,4-dioxanone-2-one, poly-1,5-dioxepan-2-one, copolymers of ethylene glycol and the above-mentioned aliphatic polyesters, copolymers of propylene glycol and the above-mentioned aliphatic polyesters), copolymers of the above-mentioned aliphatic polyesters and polyesterether, collagen and the like. Among those, copolymers of lactic acids (L form, D form, D,L form) and caprolactone are preferable, and a copolymer of L-lactic acid and ε-aprolactone is more preferable.

Preference is given to the copolymers of lactic acids/caprolactone since their dynamic properties and rates of degradation are easily controlled. Preferable molar ratios between the lactide and caprolactone in the copolymers range from 25/75 to 40/60.

The thickness of the artificial dura mater of the invention is generally 50 to 800 μm, and preferably 100 to 300 μm. When the artificial dura mater has a three-layer structure, the thickness of respective sheets on both of the outer surfaces is generally 25 to 400 μm, and preferably 50 to 150 μm. The thickness of the reinforcement disposed between the sheets is generally 20 to 500 μm, and preferably 50 to 200 μm.

The copolymers of lactide and caprolactone have an average molecular weight of about 100,000 to 500,000, preferably about 150,000 to 300,000. The polyglycolic acid has an intrinsic viscosity of about 0.8 to 1.8, preferably about 1.0 to 1.4.

The sheet of bioabsorbable synthetic polymer which constitutes the artificial dura mater of the invention preferably has smooth surfaces free from roughness. Such a sheet can be obtained by dissolving the polymer in a solvent, filtering the resultant solution and then casting the same, followed by air-drying, or forming a film by a melt-extruder and drawing the same.

Examples of non-bioabsorbable polymers include polyesters (polyethylene, polypropylene), polyurethane, fluorine-based polymers, silk, cellulose and the like. Since they are used for implantation, they should be harmless to the human body.

As described above, the invention provides an artificial dura mater which does not damage the brain surface and prevents cerebrospinal fluid leakage.

BEST MODE FOR CARRYING OUT THE INVENTION

The following examples serve to illustrate the present invention. However, the scope of the invention is not limited by these examples.

Amorphous or Low Crystallinity Polymer

EXAMPLE 1

144 g of L-lactide and 114 g of ε-caprolactone, and 100 ppm of the total weight of catalyst were placed in a glass ampoule, subjected to pressure reduction and sealed. Then, they were kept at 140° C. for 48 hours, obtaining a L-lactide/ε-caprolactone copolymer [molar ratio: 50/50; weight average molecular weight by GPC: 240,000; hereinafter referred to as P (L-LA/CL) (molar ratio: 50/50)]. Thus obtained P (L-LA/CL) (molar ratio: 50/50) was dissolved in a solvent (chloroform) so that the concentration of the solution became 5 wt %. After complete dissolution, the solution was subjected to filtration to remove insoluble matter. The solution was then cast on a glass plate (flow casting) and subjected to air drying, followed by vacuum drying at room temperature for 12 hours to remove the solvent, obtaining a composition made of P (L-LA/CL) (molar ratio: 50/50). The thickness of the obtained composition was 103 μm.

EXAMPLE 2

72 g of L-lactide and 171 g of ε-caprolactone, and 100 ppm of the total weight of catalyst were placed in a glass ampoule, subjected to pressure reduction and sealed. Then, they were kept at 140° C. for 48 hours, obtaining a L-lactide/ε-caprolactone copolymer [molar ratio: 25/75; weight average molecular weight by GPC: 200,000; hereinafter referred to as P (L-LA/CL) (molar ratio: 25/75)]. Thus obtained P (L-LA/CL) (molar ratio: 25/75) was dissolved in a solvent (chloroform) so that the concentration of the solution became 5 wt %. After complete dissolution, the solution was subjected to filtration to remove insoluble matter. The solution was then cast on a glass plate (flow casting) and subjected to air drying, followed by vacuum drying at room temperature for 12 hours to remove the solvent, obtaining a composition made of P (L-LA/CL) (molar ratio: 25/75). The thickness of the obtained composition was 94 μm.

EXAMPLE 3

144 g of L-lactide and 114 g of ε-caprolactone, and 100 ppm of the total weight of catalyst were placed in a glass ampoule, subjected to pressure reduction and sealed. Then, they were kept at 140° C. for 48 hours, obtaining a L-lactide/ε-caprolactone copolymer [molar ratio: 50/50; weight average molecular weight by GPC: 240,000; hereinafter referred to as P (L-LA/CL) (molar ratio: 50/50)]. Thus obtained P (L-LA/CL) (molar ratio: 50/50) was dissolved in a solvent (1,4-dioxane) so that the concentration of the solution became 6 wt %. After complete dissolution, the resultant solution was subjected to filtration to remove insoluble matter. The solution was then cast on a glass plate (flow casting) and subjected to lyophilization using a freeze dryer, followed by vacuum drying at 50° C. for 12 hours to remove the solvent, obtaining a spongy composition made of P (L-LA/CL) (molar ratio: 50/50). The thickness of the obtained spongy composition was 524 μm.

EXAMPLE 4

A polytetrafluoroethylene/propylene copolymer was dissolved in a solvent (THF: tetrahydrofuran) so that the concentration of the solution became 3 wt %. The solution was cast on a glass plate (flow casting) and subjected to air drying, followed by vacuum drying at 70° C. for 12 hours to remove the solvent, thus obtaining a composition made of a copolymer of polytetrafluoroethylene and propylene. The thickness of the obtained composition was 92 μm.

COMPARATIVE EXAMPLE 1

Poly-ε-caprolactone (weight average molecular weight by GPC: 80,000; hereinafter referred to as PCL) was produced in a conventional manner. The obtained PCL was dissolved in a solvent (chloroform) so that the concentration of the resultant solution became 5 wt %. After complete dissolution, the solution was subjected to filtration to remove insoluble matter. The solution was then cast on a glass plate (flow casting) and subjected to air drying, followed by vacuum drying at 40° C. for 12 hours to remove the solvent, thus obtaining a composition made of PCL. The thickness of the obtained composition was 112

Measurement of Crystallinity

The crystallinity of the compositions obtained in Examples 1, 2, 3, 4 and Comparative Example 1 was measured using an X-ray diffractometer (RAD-2C manufactured by Rigaku International Corporation). Table 1 shows the results.

TABLE 1

Crystallinity of films

| Sample | Example 1 | Example 2 | Example 3 | Example 4 | Comparative Example 1 |
|---|---|---|---|---|---|
| Crystallinity (%) | 18.6 | 12.7 | 15.4 | Unmeasurable (amorphous) | 34.3 |

Measurement of Young's Modulus at 5% Extension and Tensile Elongation at Break

The Young's modulus at 5% extension and tensile elongation at break of the compositions of Examples 1, 2, 3, 4 and Comparative Example 1 were measured using a universal tensile testing machine (AG-5000B manufactured by Shimazu Corporation) with a chuck distance of 40 mm and a stress rate of 50 mm/min. Table 2 shows the results.

Measurement of Glass Transition Point

The glass transition point of the compositions obtained in Examples 1, 2, 3, 4 and Comparative Example 1 was measured using a differential scanning calorimeter (DSC-50 manufactured by Shimazu Corporation) under a programming rate of 10° C./min. Table 2 shows the results.

Measurement of Elastic Modulus

The elastic modulus of the compositions obtained in Examples 1, 2, 3, 4 and Comparative Example 1 was measured using a non-resonant forced vibration measuring apparatus ("RHEOVIBRON"DDV-II-EA manufactured by ORIENTEC Co., Ltd.) under a driving frequency of 11 Hz and a programming rate of 0.5° C./min. Table 2 shows the results obtained at a temperature of 37° C.

Measurement of Relaxation Elastic Modulus

The relaxation elastic modulus of the compositions obtained in Examples 1, 2, 3 and Comparative Example 1 was measured by conducting a stress relaxation test at room temperature (23° C.) Table 2 shows the results and the ratio of the relaxation elastic modulus to the elastic modulus.

TABLE 2

Properties of films

| Sample | Example 1 | Example 2 | Example 3 | Example 4 | Comparative Example 1 |
|---|---|---|---|---|---|
| Young's modulus at 5% extension (MPa) | 8.12 | 5.54 | 0.63 | 0.42 | 23.64 |
| Tensile elongation at break (%) | 940 | 1065 | 446 | 250 | 49.6 |
| Glass transition point (° C.) | −17 | −50 | −17 | −38 | −60 |
| Elastic modulus ($\times 10^7$ Pa) | 2.5 | 1.6 | 0.19 | 0.87 | 24 |
| Relaxation elastic modulus ($\times 10^7$ Pa) | 2.2 | 1.1 | 0.17 | 0.30 | 3.3 |
| Relaxation elastic modulus/Elastic modulus (ratio) | 0.667 | 0.379 | 0.692 | 0.345 | 0.110 |

Pressure Tightness of Pinhole

The pressure tightness of the pinholes of the compositions obtained in Examples 1, 2, 3, 4 and Comparative Example 1 was measured in accordance with JIS L1092 (Water resistance). Table 3 shows the results.

TABLE 3

Pressure tightness of pinholes in film

| Sample | Example 1 | Example 2 | Example 3 | Example 4 | Comparative Example 1 |
|---|---|---|---|---|---|
| Pressure tightness (mmHg) | 102.9 | 81.9 | 50.0 | 73.6 | 1.94 |

These results reveal that the compositions of Examples 1, 2, 3, 4 are flexible enough to not damage the brain surface. At the same time, they are resistant to deformation since they have high ratios of relaxation elastic modulus to elastic modulus. Even when the compositions were penetrated by a suture needle, pinhole expansion was not observed. They have higher pressure tightness in their pinholes compared to that of Comparative Example 1. Intracranial pressure is generally 5 mmHg, 50 mmHg at the highest, therefore the test results show that they satisfactorily prevent cerebrospinal fluid leakage.

Preparation of Structural Reinforcement

1) Polyglycolic Acid Nonwoven Fabric

Polyglycolic acid (intrinsic viscosity=1.14) was produced in a conventional manner. The obtained polyglycolic acid was subjected to spinning to form a polyglycolic acid yarn having about 20 deniers followed by drawing, and then circular knitting the drawn yarn and needle punching this knitting. Thus, nonwoven fabric having 25 g/m² was obtained.

2) Polylactic Acid Nonwoven Fabric

Polylactic acid (weight average molecular weight by GPC: 280,000) was produced in a conventional manner. The obtained polylactic acid was subjected to spinning to form a polylactic acid yarn having about 50 deniers followed by drawing, and then circular knitting the drawn yarn and needle punching this knitting. Thus, nonwoven fabric having 38 g/m² was obtained.

3) Rayon Nonwoven Fabric

Rayon prepared by a conventional spinning method was subjected to circular knitting and needle punching to obtain nonwoven fabric. The resultant nonwoven fabric was 21 g/m².

Producing an Integral Molding

EXAMPLES 5-1 and 5-2

Each of the above-described polyglycolic acid nonwoven fabrics were inserted between the moldings obtained in Examples 1 and 2. Thereafter, the films were melted and pressed for heat fusion bonding, thus obtaining integrally molded composite films. The artificial dura maters of the invention were obtained by subjecting the films to vacuum drying at 70° C. for 12 hours. They are referred to as Examples 5-1 and 5-2, respectively.

EXAMPLE 6

The surface of the molding obtained in Example 3 was melted by spraying dioxane thereon, then the above-obtained polylactic acid nonwoven fabric was press bonded thereto, forming an integral molding. The artificial dura mater of the invention was obtained by subjecting the resultant molding to vacuum drying at 70° C. for 12 hours.

EXAMPLE 7

The rayon nonwoven fabric obtained above was inserted between the moldings of Example 1. The films were subjected to fusion press and fusion boding for obtaining an integral molding. The artificial dura mater of the invention was obtained by subjecting the resultant integral molding to vacuum drying at 70° C. for 12 hours

EXAMPLE 8

A polyglycolic acid unwoven fabric having a surface melted by hexafluoro-isopropanol was press bonded on commercially available soft polyurethane foam (thickness of 1 mm) The artificial dura mater of the invention was obtained by subjecting the resultant integral molding to vacuum drying at 70° C. for 12 hours.

EXAMPLE 9

A polytetrafluoroethylene/propylene copolymer was dissolved in a solvent (THF) and the resultant solution was cast on a glass plate (flow casting) having a rayon nonwoven fabric thereon, followed by vulcanizing air drying. The artificial dura mater of the invention was obtained by subjecting the resultant film to vacuum drying at 70° C. for 12 hours.

Tensile Strength, Young's Modulus at 5% Extension and Tensile Elongation at Break The Young's modulus at 5% extension and tensile elongation at break of the compositions of Examples 5-1, 5-2, 6, 7, 8 and 9 were measured using a universal tensile testing machine (AG-5000B manufactured by Shimazu Corporation) with a chuck distance of 40 mm and a stress rate of 50 mm/min. Table 4 shows the results.

Hydrolysis Property

The compositions of Examples 5-1, 5-2, 6, 7, 8 and 9 were observed after immersing in a physiological salt solution at 37° C. for half a year. Table 4 shows the results.

TABLE 4

| Sample | Example 5-1 | Example 5-2 | Example 6 | Example 7 | Example 8 | Example 9 |
|---|---|---|---|---|---|---|
| Tensile strength (MPa) | 15.8 | 24.1 | 2.08 | 14.1 | 0.11 | 13.8 |
| Tensile elongation at break (%) | 80 | 89.9 | 103.7 | 36.9 | 47.7 | 225 |
| Young's modulus at 5% extension (MPa) | 29.8 | 20.3 | 1.67 | 34.8 | 0.04 | 0.39 |
| Weight of nonwoven fabric (%) | 6.1 | 8.3 | 9.5 | 6.0 | 16.8 | 4.2 |
| Degradability (Hydrolysis property) | Totally deformed | Totally deformed | Form of films was almost deformed. Nonwoven fabric was weak. | Form of nonwoven fabric was retained | Form was retained | Form was retained |

The invention claimed is:

1. A method for preparing an artificial dura mater which is formed as an integral molding of an amorphous or low crystallinity polymer and a structural reinforcement, wherein the amorphous or low crystallinity polymer and the structural reinforcement are integrated by bonding, fusion or impregnation, the amorphous or low crystallinity polymer having a degree of crystallinity of 20% or lower, the amorphous or low crystallinity polymer having an elastic modulus at 5% extension of 10 MPa or lower, the amorphous or low crystallinity polymer having a Tg of 15° C. or lower, the amorphous or low crystallinity polymer having a tensile elongation at breaking of 200% or greater, the amorphous or low crystallinity polymer has an elastic modulus at 37° C. of $1 \times 10^8$ Pa or less, the amorphous or low crystallinity polymer having a ratio of relaxation elastic modulus at 23° C./elastic modulus at 37° C. of 0.3 or greater, the structural reinforcement having an elastic modulus at 5% extension of greater than 10 MPa, the structural reinforcement having a Tg of higher than 15° C., the structural reinforcement having a tensile elongation at break of less than 200%, and the amorphous or low crystallinity polymer having a weight of 10 to 98% of the total weight of the integral molding, and the structural reinforcement having a weight of 2% or more of the total weight of the integral molding, comprising the step of integrating the amorphous or low crystallinity polymer and the structural reinforcement by bonding, fusing or impregnating to give an integrally molded artificial dura mater.

2. A method for preparing an artificial dura mater of which is formed as an integral molding of an amorphous or low crystallinity polymer and a structural reinforcement, wherein the amorphous or low crystallinity polymer and the structural reinforcement are integrated by bonding, fusion or impregnation,
the amorphous or low crystallinity polymer having a degree of crystallinity of 20% or lower,
the amorphous or low crystallinity polymer having an elastic modulus at 5% extension of 10 MPa or lower,
the amorphous or low crystallinity polymer having a Tg of 15° C. or lower,
the amorphous or low crystallinity polymer having a tensile elongation at breaking of 200% or greater,
the amorphous or low crystallinity polymer has an elastic modulus at 37° C. of $1 \times 10^8$ Pa or less,
the amorphous or low crystallinity polymer having a ratio of relaxation elastic modulus at 23° C./elastic modulus at 37° C. of 0.3 or greater,
the structural reinforcement having an elastic modulus at 5% extension of greater than 10 MPa,
the structural reinforcement having a Tg of higher than 15° C.,
the structural reinforcement having a tensile elongation at break of less than 100, and
the amorphous or low crystallinity polymer having a weight of 10 to 98% of the total weight of the integral molding, and
the structural reinforcement having a weight of 2% or more of the total weight of the integral molding,
comprising the steps of:
obtaining the amorphous or low crystallinity polymer;
dissolving the polymer in a solvent to give a polymer solution;
impregnating the structural reinforcement with the polymer solution; and
removing the solvent from the impregnated structural reinforcement to form the integral molding comprising the structural reinforcement and the polymer without forming another layer in between, thereby forming said artificial dura mater.

3. A method for preparing an artificial dura mater which is formed as an integral molding of an amorphous or low crystallinity polymer and a structural reinforcement, wherein the amorphous or low crystallinity polymer and the structural reinforcement are integrated by bonding, fusion or impregnation,
the amorphous or low crystallinity polymer having a degree of crystallinity of 20% or lower,
the amorphous or low crystallinity polymer having an elastic modulus at 5% extension of 10 MPa or lower,
the amorphous or low crystallinity polymer having a Tg of 15° C. or lower,
the amorphous or low crystallinity polymer having a tensile elongation at breaking of 200% or greater,
the amorphous or low crystallinity polymer has an elastic modulus at 37° C. of $1 \times 10^8$ Pa or less,
the amorphous or low crystallinity polymer having a ratio of relaxation elastic modulus at 23° C./elastic modulus at 37° C. of 0.3 or greater,
the structural reinforcement having an elastic modulus at 5% extension of greater than 10 MPa,
the structural reinforcement having a tensile elongation at break of less than 200%, and
the amorphous or low crystallinity polymer having a weight of 10 to 98% of the total weight of the integral molding, and
the structural reinforcement having a weight of 2% or more of the total weight of the integral molding,
comprising the steps of:
dissolving the surface of a molding of a copolymer of L-lactic acid and ε-caprolactone as the amorphous or low crystallinity polymer by spraying dioxane thereon;
press-bonding a polyglycolic acid non-woven fabric as the structural reinforcement to the dissolved surface to form the integral molding; and
subjecting the integral molding to vacuum drying to give the artificial dura mater.

4. A method for preparing an artificial dura mater which is formed as an integral molding of an amorphous or low crystallinity polymer and a structural reinforcement, wherein the amorphous or low crystallinity polymer and the structural reinforcement are integrated by bonding, fusion or impregnation,
the amorphous or low crystallinity polymer having a degree of crystallinity of 20% or lower,
the amorphous or low crystallinity polymer having an elastic modulus at 5% extension of 10 MPa or lower,
the amorphous or low crystallinity polymer having a Tg of 15° C. or lower,
the amorphous or low crystallinity polymer having a tensile elongation at breaking of 200% or greater,
the amorphous or low crystallinity polymer has an elastic modulus at 37° C. of $1 \times 10^8$ Pa or less,
the amorphous or low crystallinity polymer having a ratio of relaxation elastic modulus at 23° C./elastic modulus at 37° C. of 0.3 or greater,
the structural reinforcement having an elastic modulus at 5% extension of greater than 10 MPa,
the structural reinforcement having a Tg of higher than 15° C.,
the structural reinforcement having a tensile elongation at break of less than 200%, and
the amorphous or low crystallinity polymer having a weight of 10 to 98% of the total weight of the integral molding, and the structural reinforcement having a weight of 2% or more of the total weight of the integral molding,
comprising the steps of:
inserting a rayon non-woven fabric as the structural reinforcement between two moldings of a copolymer of L-lactic acid and ε-caprolactone as the amorphous or low crystallinity polymer to form a film;
subjecting the film to fusion pressing and fusion bonding to give the integral molding; and
subjecting the integral molding to vacuum drying to give the artificial dura mater.

5. A method for preparing an artificial dura mater which is formed as an integral molding of an amorphous or low crystallinity polymer and a structural reinforcement, wherein the amorphous or low crystallinity polymer and the structural reinforcement are integrated by bonding, fusion or impregnation,
the amorphous or low crystallinity polymer having a degree of crystallinity of 20% or lower,
the amorphous or low crystallinity polymer having an elastic modulus at 5% extension of 10 MPa or lower,
the amorphous or low crystallinity polymer having a Tg of 15° C. or lower,
the amorphous or low crystallinity polymer having a tensile elongation at breaking of 200% or greater,
the amorphous or low crystallinity polymer has an elastic modulus at 37° C. of $1 \times 20^8$ Pa or less, the amorphous or low crystallinity polymer having a ratio of relaxation elastic modulus at 23° C./elastic modulus at 37° C. of 0.3 or greater, the structural reinforcement having an elastic modulus at 5% extension of greater than 10 MPa, the structural reinforcement having a Tg of higher than 15° C., the structural reinforcement having a tensile elongation at break of less than 200%, and the amorphous or low crystallinity polymer having a weight of 10 to 98% of the total weight of the integral molding, and the structural reinforcement having a weight of 2% or more of the total weight of the integral molding, comprising the steps of:

dissolving the surface of a polyglycolic acid non-woven fabric as the amorphous or low crystallinity polymer by hexafluoro-isopropanol;

press-bonding the dissolved non-woven fabric on soft polyurethane foam as the structural reinforcement; and subjecting the integral molding to vacuum drying to give the artificial dura mater.

6. A method for preparing an artificial dura mater which is formed as an integral molding of an amorphous or low crystallinity polymer and a structural reinforcement, wherein the amorphous or low crystallinity polymer and the structural reinforcement are integrated by bonding, fusion or impregnation, the amorphous or low crystallinity polymer having a degree of crystallinity of 20% or lower, the amorphous or low crystallinity polymer having an elastic modulus at 5% extension of 10 MPa or lower, the amorphous or low crystallinity polymer having a Tg of 15° C. or lower, the amorphous or low crystallinity polymer having a tensile elongation at breaking of 200% or greater, the amorphous or low crystallinity polymer has an elastic modulus at 37° C. of $1 \times 10^8$ Pa or less, the amorphous or low crystallinity polymer having a ratio of relaxation elastic modulus at 23° C./elastic modulus at 37° C. of 0.3 or greater, the structural reinforcement having an elastic modulus at 5% extension of greater than 10 MPa, the structural reinforcement having a Tg of higher than 15° C., the structural reinforcement having a tensile elongation at break of less than 200%, and the amorphous or low crystallinity polymer having a weight of 10 to 98% of the total weight of the integral molding, and the structural reinforcement having a weight of 2% or more of the total weight of the integral molding, comprising the steps of:

dissolving a polytetrafluoroethylene/propylene copolymer as the amorphous or low crystallinity polymer in a solvent to give a copolymer solution;

casting the copolymer solution on a glass plate having a rayon non-woven fabric as the structural reinforcement thereon, followed by vulcanizing air drying to form a film; and subjecting the film to vacuum drying to give the artificial dura mater.

7. The method for preparing an artificial dura mater according to claim 1, wherein the amorphous or low crystallinity polymer is biodegradable.

8. The method for preparing an artificial dura mater according to claim 1, wherein the structural reinforcement is biodegradable.

9. The method for preparing an artificial dura mater according to claim 1, wherein the amorphous or low crystallinity polymer is biodegradable and the structural reinforcement is nonbiodegradable.

10. The method for preparing an artificial dura mater according to claim 1, wherein the amorphous or low crystallinity polymer is nonbiodegradable and the structural reinforcement is biodegradable.

11. The method for preparing an artificial dura mater according to claim 2, wherein the amorphous or low crystallinity polymer is biodegradable.

12. The method for preparing an artificial dura mater according to claim 2, wherein the structural reinforcement is biodegradable.

13. The method for preparing an artificial dura mater according to claim 2, wherein the amorphous or low crystallinity polymer is biodegradable and the structural reinforcement is nonbiodegradable.

14. The method for preparing an artificial dura mater according to claim 2, wherein the amorphous or low crystallinity polymer is nonbiodegradable and the structural reinforcement is biodegradable.

* * * * *

UNITED STATES PATENT AND TRADEMARK OFFICE
CERTIFICATE OF CORRECTION

PATENT NO. : 7,041,713 B2
APPLICATION NO. : 10/019754
DATED : May 9, 2006
INVENTOR(S) : Yamauchi et al.

It is certified that error appears in the above-identified patent and that said Letters Patent is hereby corrected as shown below:

At column 12, line 67, please delete "$1 \times 20^8$" and insert therefore, --$1 \times 10^8$--.

Signed and Sealed this
Twenty-eighth Day of February, 2012

David J. Kappos
*Director of the United States Patent and Trademark Office*